United States Patent [19]

Hanlon et al.

[11] Patent Number: 5,344,468
[45] Date of Patent: Sep. 6, 1994

[54] ORGANIC PHOSPHATES AND THEIR USE AS WEAR INHIBITORS

[75] Inventors: J. Vincent Hanlon, St. Louis, Mo.; John G. Bostick, Smithton, Ill.; Charles H. Kolich, Baton Rouge, La.

[73] Assignee: Ethyl Petroleum Additives, Inc., Richmond, Va.

[21] Appl. No.: 949,734

[22] Filed: Sep. 23, 1992

Related U.S. Application Data

[63] Continuation of Ser. No. 715,674, Jun. 14, 1991, abandoned.

[51] Int. Cl.$^5$ ............................................. C10L 1/26
[52] U.S. Cl. ................................................. 44/379; 44/382
[58] Field of Search ................................. 44/379, 382

[56] References Cited

U.S. PATENT DOCUMENTS

| | | | |
|---|---|---|---|
| 2,071,323 | 2/1937 | Bass | 260/99.20 |
| 2,291,442 | 7/1942 | Bass et al. | 44/58 |
| 3,077,491 | 2/1963 | Seglin et al. | 260/461 |
| 3,232,724 | 2/1966 | Finnigan et al. | 44/66 |
| 3,658,497 | 4/1972 | Sung et al. | 44/69 |
| 3,780,145 | 12/1973 | Malec | 260/966 |
| 3,807,974 | 4/1974 | Kerley et al. | 44/58 |
| 3,965,220 | 6/1976 | Schumacker | 260/975 |
| 4,033,887 | 7/1977 | De Roocker | 252/49.8 |
| 4,087,386 | 5/1978 | Dounchis | 252/49.8 |
| 4,444,649 | 4/1984 | Dvoracek | 208/48 AA |
| 4,612,127 | 9/1986 | Uematsu et al. | 252/32.5 |
| 4,705,879 | 11/1987 | Dressler | 558/194 |

Primary Examiner—Margaret Medley
Attorney, Agent, or Firm—John F. Sieberth

[57] ABSTRACT

Compositions comprising a hydrocarbonaceous middle distillate fuel and a minor wear-inhibiting amount of a combination of (i) at least one fuel-soluble aryl phosphate of the formula $$(RO)_3PO$$

wherein each R is, independently, phenyl or an alkyl-substituted phenyl group; and (ii) at least one fuel-soluble aryl polyphosphate of the formula

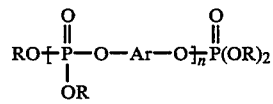

wherein each R is, independently, phenyl or an alkyl-substituted phenyl group, Ar is m-phenylene or an alkyl-substituted m-phenylene group, and n is from 1 to 4. The combination contains from 2 to 30% by weight of component (i). These compositions are made by (a) reacting about 1.9 to about 2.1 equivalents of phenol or alkyl-substituted phenol with one equivalent of phosphoryl trihalide, and (b) reacting the intermediate product formed in (a) with from about 0.9 to about 1.1 equivalents of resorcinol or alkyl-substituted resorcinol per equivalent of phosphoryl trihalide employed in (a). Alternatively, the compositions are made by (a) reacting about 0.9 to about 1.1 equivalents of resorcinol or alkyl-substituted resorcinol with one equivalent of phosphoryl trihalide, and (b) reacting the intermediate product formed in (a) with from about 1.9 to about 2.1 equivalents of phenol or alkyl-substituted phenol per equivalent of phosphoryl trihalide employed in (a).

24 Claims, No Drawings

ORGANIC PHOSPHATES AND THEIR USE AS WEAR INHIBITORS

This application is a continuation of application Ser. No. 715,674, filed Jun. 14, 1991 now abandoned.

This invention relates to the use of novel organic phosphate ester combinations as wear inhibitors in middle distillate engine fuels, especially hydrocarbonaceous fuels for diesel, jet or gas turbine engines.

A need exists for ashless (i.e., metal-free) wear inhibitors for use in middle distillate fuels, such as diesel fuels and especially hydrocarbonaceous fuels for use in gas turbine or jet engines such as are employed in military and civilian aircraft. Fuels of this type are subjected to high temperatures during actual service conditions. Thus in a jet or gas turbine fuel, the wear inhibitor must not only be capable of inhibiting wear but must be capable of exerting such effectiveness even while exposed to high temperatures.

This invention provides, in one of its embodiments, a combination of aryl phosphates deemed suitable for use in fulfilling the aforesaid need. The combination is composed of (i) at least one fuel-soluble aryl phosphate of the formula

(RO)₃PO wherein each R is, independently, phenyl or an alkyl-substituted phenyl group; and (ii) at least one fuel-soluble aryl polyphosphate of the formula

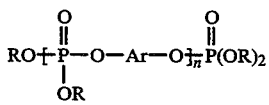

wherein each R is, independently, phenyl or an alkyl-substituted phenyl group, Ar is m-phenylene or an alkyl-substituted m-phenylene group, and n is a whole or fractional number from 1 to 4; said combination containing from 2 to 30% by weight of component (i). When the above formula represents a mixture of the depicted polypnosphates, n is a whole or fractional number from 1 to 4, as n represents the average composition of the mixture.

Among the advantages of these combinations is the ease with which they can be formed. In particular, the foregoing combinations can be formed by a process which comprises (a) reacting from about 1.9 to about 2.1 moles of phenol and/or alkyl-substituted phenol with one mole of phosphoryl trihalide in the presence of a Lewis acid catalyst, and (b) reacting the intermediate product formed in (a) with from about 0.45 to about 0.55 moles of resorcinol and/or alkyl-substituted resorcinol per mole of phosphoryl trihalide employed in (a) again in the presence of a Lewis acid catalyst. Although other modes of addition can be used, it is preferable in (a) to add the phenol and/or alkyl-substituted phenol to the phosphoryl trihalide, and in (b) to add the resorcinol and/or alkyl-substituted resorcinol to the intermediate product formed in (a). Nonlimiting examples of suitable Lewis acid catalysts include AlCl₃, AlBr₃, FeCl₃, FeBr₃, BCl₃, PCl₅, and MgCl₂. In an alternate process, the Lewis acid catalyst is replaced by a stoichiometric amount of a hydrogen halide acceptor and a solvent is used. In step (a) a solution of phenol and/or an alkyl-substituted phenol and hydrogen halide acceptor is added to a solution of the phosphoryl trihalide, and in step (b) a solution of resorcinol and/or an alkyl-substituted resorcinol and hydrogen halide acceptor is added to the intermediate product formed in step (a).

In still another process, the foregoing combinations are formed by (a) reacting from about 0.45 to about 0.55 moles of resorcinol and/or alkyl-substituted resorcinol with one mole of phosphoryl trihalide in the presence of a Lewis acid catalyst, and (b) reacting the intermediate product formed in (a) with from about 1.9 to about 2.1 moles of phenol and/or alkyl-substituted phenol per equivalent of phosphoryl trihalide employed in (a) again in the presence of a Lewis acid catalyst. Although other modes of addition can be used, it is preferable in (a) and in (b) to add the resorcinolic and the phenolic reactants to the phosphoryl trihalide and to the reaction mixture formed in (a), respectively. In an alternate process, the Lewis acid catalyst is replaced by a stoichiometric amount of a hydrogen halide acceptor and a solvent is used. In step (a) a solution of resorcinol and/or an alkyl-substituted resorcinol and hydrogen halide acceptor is added to a solution of the phosphoryl trihalide, and in step (b) a solution of phenol and/or an alkyl substituted phenol and hydrogen halide acceptor is added to the intermediate product formed in step (a).

In each of the above processes, it is preferred to employ the reactants in proportions such that there are at least 3.1 equivalents of ar-hydroxy groups (phenolic reactant plus resorcinolic reactant) per equivalent of phosphoryl trihalide used.

The above phosphate combinations and their syntheses form the subject of copending application Ser. No. 07/715,686, filed concurrently herewith by one of us (CHK) now pending.

The use of the above phosphate combinations as antiwear additives in lubricating oils and functional fluids forms the subject of our copending application Ser. No. 07/715,675, now abandoned.

This invention provides a middle distillate fuel composition which comprises a major proportion of a hydrocarbonaceous middle distillate fuel and a minor wear-inhibiting amount of a combination of phosphate esters (i) and (ii) as described herein above. The fuel compositions are of primary usefulness as engine fuels where wear inhibition is of particular importance. Thus in one embodiment the base fuel used is a fuel adapted for use in gas turbine and jet engines. In another embodiment the base fuel used is a fuel adapted for use in the operation of diesel engines. The fuels of this invention can however be used as heating oils or burner fuels.

In the above formulas, most preferably each R is phenyl or alkyl phenyl (preferably alkyl phenyl groups in which the alkyl group has 2 to 10 carbon atoms) and Ar is m-phenylene. Likewise, it is preferred that at least 50% by weight of the aryl poiyphosphate corresponds to the above formula of component (ii) wherein n is 1. Particularly preferred are (1) compositions wherein each R is phenyl and at least 50% by weight of the aryl polyphosphate is m-phenylenebis(diphenyl phosphate), and (2) compositions wherein at least 60% by weight of the combination of phosphate esters is a combination of m-phenylenebis(diphenyl phosphate) and triphenyl phosphate in a weight ratio of 1 to 35 parts of m-phenylenebis(diphenyl phosphate) per each part by weight of triphenyl phosphate.

The above and other embodiments of this invention will be still further apparent from the ensuing description and appended claims.

In forming the combination of aryl phosphates, use can be made of phenol and/or one or more alkyl phenols which contain from 1 to 5 alkyl groups on the ring. Each such alkyl group can contain up to about 18 carbon atoms (preferably up to about 6 carbon atoms, and more preferably each alkyl group is methyl) with the proviso that the alkyl substituent(s) should not sterically hinder the hydroxyl group to such an extent that the substituted phenol is incapable of reacting with the phosphoryl trihalide. Examples of suitable alkyl phenols include o-, m- and/or p-cresol; 2,3-, 2,4-, 2,5-, 2,6-, 3,4-, and/or 3,5-xylenol; o-, m-, and p-ethylphenol; p-tert-butylphenol; p-tert-amylphenol; p-(1,1,3,3-tetramethylbutyl)phenol; p-nonylphenol; p-decylphenol; 2,4,5-trimethylphenol; 2,3,4,5-tetramethylphenol; pentamethylphenol, etc. Cycloalkylphenols such as p-cyclohexylphenol can also be used. Mixtures of two or more different phenols are also suitable. Use of phenol itself or monoalkyl phenols in which the alkyl group has 2 to 10 carbon atoms is most preferred.

The phosphoryl trihalide used in forming the phosphate combinations is preferably phosphoryl trichloride, but other halides such as the tribromide can be used.

Resorcinol is the preferred dihydroxybenzene reactant used in forming the phosphate combinations. However alkyl-substituted resorcinols can be used again with the proviso that the compounds are not so sterically hindered as to be unable to undergo reaction on both hydroxyl groups with the intermediate formed from the reaction between the monohydric phenol and phosphoryl trihalide. A few examples of alkyl-substituted resorcinols that can be used include 5-alkyl-1,3-dihydroxybenzenes where the alkyl group has 1 to about 18 carbon atoms; 2-methyl-1,3-dihydroxylbenzene; 4-methyl-1,3-dihyroxybenzene; 4,5-dimethyl-1,3-dihydroxybenzene; and the like.

The reactions of (a) and (b) above are usually conducted at temperatures in the range of about 30° C. to about 200° C. It is desirable and most economical to conduct these reactions without a solvent and in the presence of a catalytic amount of a Lewis acid. However, a suitable inert liquid solvent such as toluene, xylene, aromatic naphtha, or the like can be used.

The amount of catalyst used is typically between 0.1 wt % and 10 wt % based upon the amount of phosphoryl trihalide. More preferred is 0.5 wt % to 5.0 wt % and most preferred is 0.75 wt % to 2.00 wt %.

In place of the Lewis acid catalyst, an at least stoichiometric amount of a hydrogen halide acceptor can be used. Hydrogen halide acceptors which are preferably used in the reactions of (a) and (b) above are typified by tertiary amines such as pyridine, pyrimidine, pyrazine, triethylamine, tributylamine, and triphenylamine. Other known hydrogen halide acceptors are usable, however. It is most desirable to use an inert solvent for the reactions involving hydrogen halide acceptors in order to facilitate handling of the solid hydrohalide by-product. Suitable solvents are toluene, xylene, aromatic naphtha, or the like.

The following examples illustrate various phosphate combinations used pursuant to this invention, and methods which can be used for their synthesis.

EXAMPLE 1

A 912.87 g (9.70 mole) portion of phenol (Aldrich, redistilled) and a 766.65 g (5.00 mole) portion of POCl$_3$ (Aldrich, 99%) were weighed into a dry, four-necked 5-L flask in a glove box. The flask was then set-up in a hood with a mechanical paddle stirrer, a thermometer, a glycol-cooled Friedrich condenser, an oil bath, and a rubber septum addition port. Exit gases from the condenser were passed through a trap and into an aqueous NaOH scrubber solution located on a balance. A slow nitrogen purge was maintained into the contents of the flask by a Teflon tube inserted through the rubber septum addition port.

The brownish-gold solution was warmed to 33° C. by the oil bath, and 15.42 g (2.01 wt % based on POCl$_3$) of AlCl$_3$ (Aldrich) catalyst was cautiously added. The solution was slowly heated to 116° C. over a seven hour period while 344.9 g of HCl (97.5% of theory) collected in the exit gas scrubber. The solution was then cooled to room temperature, and a 291.79 g (2.65 mole) portion of resorcinol (Aldrich, recrystallized) was added (in a glove box). The reddish-purple mixture was then slowly heated to 170° C. over a five and one-half hour period while 172.1 g of HCl (89.1% of theory) collected in the scrubber.

The viscous golden-yellow crude product was dissolved in toluene (2544.5 g), and the solution was shaken with 10 wt % aqueous NaOH (2×1000 g) and then tap water (3×1000 g) to obtain 3840.4 g of cloudy colorless organic phase. The solution was then dried over 125 g of anhydrous MgSO$_4$. The liquid was decanted from the drying agent and passed through a bed (28 mm O.D. by 364 mm length) of 101.0 g activated silica gel (Aldrich, 70–230 mesh, 500 M$^2$/g, wet packed using toluene). The eluate was then stripped on a rotary evaporator (95° C./0.1 torr) to obtain 1242.7 g (87.2% yield) of a slightly hazy, pale yellow fluid. This liquid was pumped through a 10-micron Teflon membrane filter to obtain 1227.67 g of a clear pale yellow product, properties of which are summarized in Table I hereinafter.

EXAMPLE 2

A 77.24 g (0.5037 mole) portion of POCl$_3$ (Aldrich) and 148.6 g toluene were weighed into a 1-L four-necked flask in a glove box. The flask was set-up in a hood and equipped with a paddle stirrer, thermometer, 500-mL addition funnel, and a glycol-cooled Friedrich condenser attached to a nitrogen bubbler. The flask was cooled with an ice bath while a solution of 90.07 g (0.957 mole) phenol (Aldrich, redistilled), 99.64 g (0.986 mole) triethylamine (TEA, Aldrich), and 101.94 g toluene was added from the additional funnel in 2.5 hr at 3°–15° C. After stirring for 15 minutes at 7°–15° C., a hot (70°–90° C.) clear blue solution of 30.51 g (0.277 mole) resorcinol (Aldrich, recrystallized) in 118.19 g (1.170 mole) TEA was pressured into the reaction flask through a stainless steel transfer needle from a capped bottle in 13 minutes at 15°–29° C. The reaction mixture was stirred for 2.2 hr at 23°–32° C., and then 202.7 g of 5 wt % aqueous HCl was added followed by 39.6 g concentrated hydrochloric acid. The mixture was transferred to a separatory funnel, and the lower hazy yellow aqueous layer (514.8 g, pH 1-2) was removed. After washing with water (3×225 g), the cloudy organic phase (513.6 g) was dried over 10.1 g anhydrous magnesium sulfate. Upon standing for 16 hr, the addition of 6.8 g of activated silica gel (Aldrich, 70–230 mesh, 500 m$^2$/g) immediately reduced the color of the yellow liquid. The mixture was gravity filtered through paper, and the pale-yellow filtrate was stripped on a rotary evaporator (100° C./1 torr) to obtain 131.3 g (92% yield)

of hazy light-yellow fluid. A clear liquid was obtained after pumping the product through a 10-micron membrane filter. Table I, presented hereinafter, summarizes the properties of this product.

EXAMPLE 3

This experiment was conducted as described in Example 1. A 184.46 g (1,960 mole) portion of phenol was combined with 153.33 g (1,000 mole) of $POCl_3$ in a 500-mL four necked-flask. The pale-yellow solution was warmed to 38° C., and 3.075 g (2.0 wt % based on $POCl_3$) of $MgCl_2$ was added, the pale-orange solution was then slowly heated with an electric mantle for 8.0 hr to a final temperature of 150° C. The caustic scrubber for the exit gases from the reaction increased in weight by 65.1 g (91% theory for HCl). The reaction flask was transferred to a glove box where 57.26 g (0.520 mole) of white resorcinol (Aldrich, recrystallized) was added. The mixture was then slowly heated over three and one-half hours to a final temperature of 140° C. with the subsequent increase in the exit gas scrubber weight of 32.7 g (86.2% of theory for HCl). The dark brown viscous liquid (287.33 g) was dissolved in 557.29 g toluene and washed in a 2-L separatory funnel with 5.2 wt % aqueous NaOH (2×250 g). The organic phase was then washed with tap water (3×275 g) until the recovered aqueous phase reached a pH of 7. The cloudy organic phase was dried over anhydrous magnesium sulfate (30.46 g). The mixture was then gravity filtered through paper, and the clear, nearly colorless filtrate was stripped of solvent on a rotary evaporator (0.1 torr/90° C.) to obtain 202.2 g (70.8% yield) of a slightly hazy pale-yellow fluid. The liquid was pumped through a 10-micron Teflon membrane filter to obtain 193.36 g of a clear pale-yellow product. Properties of this sample are summarized in Table I below.

EXAMPLE 4

A 376.44 g (4.00 mole) portion of phenol is combined with 306.66 g (2.00 mole) of $POCl_3$ in a 1-L four necked flask in a glove box. The light-orange solution is warmed to 40° C. and 2.993 g (1.0 wt % based on $POCl_3$) of pyridine (Baker) is added. The solution is heated with an electric mantle until gas evolution stops (11.0 hr/145° C.). The exit gas scrubber shows a weight increase of 139.8 g (95.9% of theory for HCl).

A 114.51 g (1.04 mole) portion of resorcinol is added to the light-yellow reaction mixture in a glove box. The solution is heated to 30° C. and 3.062 g (1.0 wt % based on $POCl_3$) of magnesium chloride is added. The rusty-brown solution is heated until gas evolution stops (7.0 hr/149° C.). The subsequent increase in the exit gas scrubber is 64.0 g (84% of theory for HCl). The light-yellow viscous liquid is dissolved in 1070 g toluene. The solution is washed in a 4-L separatory funnel with dilute (2.8 wt %) aqueous NaOH (2×290 g) and then water (3×400 g). The cloudy organic phase is gravity filtered through paper to obtain a clear colorless filtrate. The filtrate is stripped on the rotary evaporator (0.1 torr/95° C.) to obtain 484.8 g (84.4% yield) of pale yellow cloudy liquid. The liquid is pumped through a 10-micron Teflon membrane filter to obtain 472.5 g of clear product. Properties of this sample are given in Table I.

EXAMPLE 5

A 188.56 g (2.00 moles) portion of phenol (Aldrich, redistilled) was combined with 153.35 (1.00 mole) of $POCl_3$ (Aldrich) in a 500-mL four-necked flask. The clear light-brown solution was warmed to 35° C., and 3.039 g (1.98 wt % based on $POC_3$) of aluminum chloride (Aldrich) was added. A small exotherm increased the temperature to 42° C. as HCl evolution began. The clear red solution was then slowly heated with an electric mantle for 5 hours to a final temperature of 109° C. The caustic scrubber for the exit gases from the reaction increased in weight by 70.4 g (96.5% of theory for HCl). The reaction flask was transferred to a glove box where 55.04 g (0.500 mole) of resorcinol (Aldrich, recrystallized) was added. The mixture was then slowly heated over 7 hours to a final temperature of 158° C. with the subsequent increase in the exit gas scrubber weight of 33.8 g (92.7% of theory for HCl). The light-orange viscous liquid (289.0 g) was dissolved in 467.8 g toluene and washed in a 2-L separatory funnel with 10 wt % aqueous NaOH (2×200 g). The cloudy organic phase was then washed with tap water (4×200g) until the recovered aqueous phase reached a pH of 6.5. The cloudy organic phase was dried over anhydrous magnesium sulfate (11.5 g). The mixture was then gravity filtered through paper, and the clear, nearly colorless filtrate was stripped of solvent on a rotary evaporator (0.1 torr/90° C.) to obtain 252.7 g (87.9% yield) of a slightly hazy pale-yellow fluid. The liquid was pumped through a 10-micron Teflon membrane filter to obtain 241.6 of clear pale-yellow product. The properties of this product are summarized in Table I.

TABLE I

| Properties | Ex. 1 | Ex. 2 | Ex. 3 | Ex. 4 | Ex. 5 |
| --- | --- | --- | --- | --- | --- |
| Composition (HPLC wt %) | | | | | |
| Triphenyl phosphate | 12.6 | 2.3 | 11.0 | 11.9 | 14.7 |
| Diphosphate | 57.2 | 78.1 | 66.0 | 65.8 | 63.4 |
| APHA Color | 50–60 | 300 | 150 | 60 | 60 |
| Viscosity at 25° C., cp | 425 | 551 | 397 | 326 | 345 |
| Density at 25° C., g/mL | 1.293 | 1.297 | 1.292 | 1.288 | 1.288 |
| Acid Number, mg KOH/g | 0.17 | 0.98 | 0.46 | 0.75 | 0.09 |
| Ionic Cl, ppm | 0.5 | 6 | 12 | 1.5 | <1.0 |

EXAMPLE 6

This experiment was carried out as described in Example 1. A 384.6 g (1.75 mole) portion of nonylphenol was combined with 137.94 g (0.8996 mole) $POCl_3$ in a 1-L four-necked flask. A 2.78 g (0.0208 mole) portion of $AlCl_3$ was added to the mixture at 29° C., and the mixture was heated to 118° C. over 3 hr. After cooling to room temperature, a 52.5 g (0.477 mole) portion of resorcinol was added to the reaction mixture. The reaction was completed by heating to 170° C. in 2.5 hr. After cooling to 45° C., toluene (4323.4 g) was added, and the solution was washed with 10 wt % aqueous NaOH (200 g) and twice with water. To obtain good phase separation for the last wash, the pH had to be adjusted to 10 with addition of aqueous NaOH. The organic phase was dried over anhydrous $MgSO_4$ (25.7 g), gravity filtered through paper, and the filtrate stripped on a rotary evaporator (0.1 torr/100° C.) to obtain 458.0 g (96.1% yield) of pale-yellow oil. Properties are summarized in Table II below.

EXAMPLE 7

Example 6 was repeated replacing the nonylphenol with a mixture of phenol (91.30 g, 0.970 mole) and nonylphenol (213.75 g, 0.970 mole). A 153.32 g (1.00 mole)

portion of POCl₃, 58.36 g (0.530 mole) resorcinol and 3.130 g (0.023 mole) AlCl₃ were used. The pale-yellow liquid product weighed 379.3 (93.1% yield). Table II sets forth physical properties of this product.

EXAMPLE 8

A 55.1 g (0.50 mole) portion of resorcinol (MCB, recrystallized, 99.93 area % by GC) was weighed into a dry four-necked 1-L flask in a glove box. The flask was then set-up in a hood with a mechanical paddle stirrer, a thermometer, a rubber septum addition port, and a Friedrich water condenser. Exit gases from the condenser were passed through a dry glass trap and into an aqueous NaOH scrubber solution located on a balance. A slow nitrogen flow was maintained on the exit gas line during the reaction to prevent back-up of the scrubber solution.

A 153.3 g (1.00 mole 93 ml) portion of POCl₃ (Aldrich, 99%) was added to the flask by nitrogen pressure from a septum capped bottle using a stainless steel transfer needle. The easily stirred slurry was heated to 113° C. with less than 0.3 g of HCl being collected in the exit gas scrubber. After cooling to 40° C., a 1.493 g (0.0112 mole) portion of anhydrous AlCl₃ (Aldrich) catalyst was added to the purple-brown liquid. The solution was slowly heated to 110° C. in 90 minutes while 37.5 g of HCl collected in the exit gas scrubber. The yellow-brown mixture was cooled to 63° C. and a 194.2 g (2.064 mole) portion of phenol (Aldrich, redistilled) was added in 15 min. The solution was heated to 155° C. in 2 hr while an additional 66.0 g (94.6% of theory for HCl) of HCl was collected in the scrubber. Addition of another 0.93 g (0.0070 mole) AlCl₃ at 120°–129° C. did not cause release of additional HCl.

The viscous yellow-brown crude product (293.4 g) was dissolved in toluene (446.7 g), and the solution was washed with 5 wt % aqueous NaOH (3×200 g) and water (2×230 g).

The cloudy pale-yellow organic phase (722.2 g) was dried over 15.17 g of anhydrous magnesium sulfate. The mixture was gravity filtered through paper (Whatman 2V), and the clear filtrate was stripped on a rotary evaporator (95° C./0.1 torr) to obtain 60.1 g (90.5% yield) of a slightly hazy, viscous, light-yellow liquid. The liquid was pumped through a 10 micron Teflon membrane filter to remove the hazy appearance. Properties of this product are summarized in Table II below.

EXAMPLE 9

Example 8 was repeated using the same reagents but with a higher level of resorcinol. Phosphoryl chloride (153.5 g, 1.001 mole) was added to resorcinol (66.15 g, 0.6008 mole) at 25° C. in 5 minutes. The temperature dropped to 20° C., and there was no evidence of HCl evolution from the easily stirred slurry. A 1.561 g (0.0117 mole) portion of anhydrous AlCl₃ was added, and the mixture was warmed gently with an electric mantle. At 30° C., HCl evolution began slowly and nearly all solids had dissolved in the red-brown liquid. Gas evolution continued at 60°–80° C. for 1 hr. A weight increase of 44.0 g was recorded for the exit gas scrubber, and the solution color changed to yellow-brown. Liquid phenol (193.2 g, 2.053 mole) was then added 5 minutes at 70°–77° C. The mixture was held at 72°–78° C. for 2.5 hr during which the scrubber weight increase rose to 99.0 g (90% of theory for HCl ). The solution was then heated to 122° C. in 2 hr with the scrubber weight gain reaching a constant value of 103.5 g (94.5% of theory). The clear orange liquid was sparged with nitrogen overnight at ambient temperature. A solution of the crude product (299.5 g) in toluene (449.4 g) was washed with 10 wt % aqueous NaOH (4×200 g) and then deionized water (3×300 g) to obtain 697.9 g of a cloudy colorless organic phase. The solution was dried over 16.3 anhydrous MgSO₄, gravity filtered through paper, and stripped on a rotary evaporator to obtain 238.1 g (84.8% yield) of a slightly hazy, nearly colorless viscous liquid. The liquid was pumped through a 10 micron Teflon membrane filter to remove the hazy appearance.

Properties of the products formed in Examples 6–9 are summarized in Table II.

TABLE II

| Properties | Ex. 6 | Ex. 7 | Ex. 8 | Ex. 9 |
|---|---|---|---|---|
| Composition (HPLC wt %) | | | | |
| Triphenyl phosphate | — | — | 17.4 | 9.2 |
| Diphosphate | — | — | 24.6 | 22.4 |
| APHA Color | — | — | 100 | 100–200 |
| Viscosity at 25° C., cp | 111,400 | 10,350 | 488 | 1270 |
| Density at 25° C., g/mL | 1.051 | 1.129 | 1.296 | 1.312 |
| Acid Number, mg KOH/g | 0.10 | 0.07 | 0.41 | 0.07 |
| Ionic Cl, ppm | 27 | 330 | <40 | 97 |

The excellent thermal stability of the phosphate combinations utilized in the practice of this invention was illustrated by a series of thermogravimetric analyses in which weight loss of various phosphorus-containing materials was determined in the range of up to 600° C. Subjected to this test were the phosphate combination produced as in Example 1, in Example 6, and in Example 7. For comparative purposes TGA analyses were also conducted on samples of tri-n-octyl phosphate (TOP), tricresyl phosphate (TCP), tri-n-butoxyethyl phosphate (TBEP), and cresyl diphenyl phosphate (CDP). The results of these determinations are summarized in Table III.

TABLE III

| Phosphorus Compound | TGA, % LOSS Temperature, °C. | | | | | | |
|---|---|---|---|---|---|---|---|
|  | 100 | 200 | 300 | 350 | 400 | 500 | 600 |
| Example 1 | 0.0 | 1.3 | 15.8 | 39.0 | 77.8 | 97.4 | 98.8 |
| Example 6 | 0.0 | 0.6 | 4.8 | 8.4 | 20.2 | 81.5 | — |
| Example 7 | 0.0 | 0.6 | 4.3 | — | 23.9 | 92.9 | — |
| TOP | 0.0 | 3.3 | 98.3 | — | 98.7 | — | — |
| TCP | 0.0 | 1.2 | 76.3 | — | 99.1 | — | — |
| TBEP | 0.5 | 2.4 | 96.5 | — | 97.1 | — | — |
| CDP | 0.0 | 1.4 | 88.0 | — | 99.5 | 99.6 | — |

The performance improvements achievable by the practice of this invention are illustrated by the results obtained in a series of standard tests known as the ball on cylinder lubricity evaluation test. The test procedure is ASTM D 5001-90. In these tests scar diameter measurements are taken, and thus the smaller the scar diameter, the more effective the additive composition as regards wear inhibition. For convenience, the results are herein expressed in numerical values representing the scar diameter in millimeters multiplied by 100.

In a first series of tests the aryl phosphate combination formed as in Example 5 was blended into a commercially-available jet fuel at a concentration of 25 pounds per thousand barrels (ptb). This blended fuel was stored at 77° F. under ambient light conditions for two months prior to conducting the lubricity test, to be sure that the fuel composition had good storage stability. The clear base fuel in this test showed a scar diameter of 67 whereas the fuel containing the phosphate combination of this invention exhibited a scar diameter of 44.

In another such test the base fuel had a scar diameter of 60 whereas the presence therein of 80 parts per million (ppm) of a combination formed as in Example 4 reduced the scar diameter to 40.

Another series of such lubricity tests were conducted wherein the base fuel was a commercial JP-4 jet fuel. This fuel as received gave a scar diameter of 60. The presence in the fuel of an aryl phosphate combination produced as in Example 5 at the level of 25 ptb gave a scar diameter of 46. It is interesting to note that the presence in the same base fuel of comparable concentrations of tricresyl phosphate, trioctyl phosphate, and tributoxyethyl phosphate gave, respectively, scar diameters of 80. 80 and 83.

When the lubricity test was applied to a series of fuels based on a low sulfur grade of commercially-available diesel fuel, the following results were obtained:

| Fuel composition | Scar diameter |
| --- | --- |
| Base fuel | 65 |
| Base fuel + 25 ptb combination per Example 5 | 47 |
| Base fuel + 25 ptb tricresyl phosphate | 64 |
| Base fuel + 25 ptb trioctyl phosphate | 65 |
| Base fuel + 25 ptb tributoxyethyl phosphate | 66 |

Another series of lubricity tests was carried out using commercially-available jet fuel. The test results are tabulated below.

| Fuel composition | Scar diameter |
| --- | --- |
| Base fuel | 68 |
| Base fuel + 25 ptb combination per Example 5 | 56 |
| Base fuel + 25 ptb tricresyl phosphate | 67 |
| Base fuel + 25 ptb trioctyl phosphate | 68 |
| Base fuel + 25 ptb tributoxyethyl phosphate | 72 |

A group of tests were conducted in which two different aryl phosphate combinations were blended into a commercially-available jet fuel at several different concentration levels. One such additive combination was produced as in Example 5 and thus, referring to the formulas given above, R was phenyl and Ar was m-phenylene. In the other such additive combination, R was nonylphenyl and Ar was m-phenylene. The results of these tests are presented below wherein "Combination A" refers to the combination wherein R was phenyl, and "Combination B" refers to the combination wherein R was nonylphenyl:

| Fuel composition | Scar diameter |
| --- | --- |
| Base fuel | 73 |
| Base fuel + 80 ppm Combination A | 39 |
| Base fuel + 40 ppm Combination A | 56 |
| Base fuel + 20 ppm Combination A | 67 |
| Base fuel + 10 ppm Combination A | 69 |
| Base fuel + 80 ppm Combination B | 68 |
| Base fuel + 40 ppm Combination B | 67 |
| Base fuel + 20 ppm Combination B | 68 |
| Base fuel + 10 ppm Combination B | 68 |

The phosphate combinations of this invention can be used as antiwear agents in any middle distillate fuel suitable for use in the operation of a jet engine, a gas turbine engine or a diesel engine. Such fuels are predominantly hydrocarbonaceous in composition and are typically characterized by boiling in the range of about 130° C. to about 400° C. It is to be noted that the term "middle distillate fuel" is not intended to be restricted to straight-run distillate fractions. These middle distillate fuels or fuel oils can comprise straight run distillate fuel oils, catalytically or thermally cracked (including hydrocracked) distillate fuel oils, or mixtures of straight run distillate fuel oils, naphthas and like stocks, with cracked distillate stocks. Moreover, such fuel oils can be treated in accordance with well known operations such as acid or caustic treatment, hydrogenation, solvent refining, clay treatment, and the like. The base fuels thus include diesel fuels, kerosenes, jet fuels, gas oils, cycle oils etc. While derived principally from petroleum, the fuels can be derived at least in part from shale, tar sands, coal, lignite, biomass, and similar sources. The fuels can contain suitable oxygenated blending components, such as alcohols, ethers, etc, including in situ produced oxygenates.

The phosphate combinations can also be used as wear inhibitors in fuels which are non-hydrocarbonaceous or substantially non-hydrocarbonaceous, such as, for example, in fuels of the type set forth in U.S. Pat. Nos. 4,177,768; 4,185,594; 4,198,931; 4,204,481; 4,208,190; 4,227,889; 4,242,099; 4,248,182; 4,448,586; 4,508,540; 4,892,561 and 4,929,252.

In general, the compositions of this invention are employed in the base fuel in an amount at least sufficient to inhibit wear between contacting metal surfaces. Ordinarily, such amounts will fall within the range of from about 0.005 to about 5 percent by weight of the base fuel, and more typically within the range of from about 0.05 to about 2 percent by weight based on the weight of the base fuel.

Various additional additives may be used in the fuels of this invention. These include antioxidants, conductivity improvers (also known as static dissipator additives), metal deactivators, icing inhibitor additives, cetane improvers, combustion improvers (including smoke suppressants), detergent/dispersant additives, induction system cleanliness agents, corrosion inhibitors, demulsifying agents, top cylinder lubricants, dyes, and the like.

Of the antioxidants, use of phenolic antioxidants is preferred, although other fuel-soluble antioxidants are available and can be used. Typical fuel-soluble antioxidants that can be, and preferably are, included in the fuels of this invention include 2,6-di-tert-butylphenol, 4-methyl-2,6-di-tert-butylphenol, 6-tert-butyl-2,4-dimethylphenol, a mixture composed of at least 75% by weight of 2,6-di-tert-butylphenol and up to 25% by weight of mono-tert-butylphenols and tri-tert-butylphenols, a mixture composed of at least 72% by weight of 6-tert-butyl-2,4- dimethylphenol and up to 28% by weight of mono-tert-butylphenols and other tert-butyl-dimethylphenols, 4-ethyl-2,6-di-tert-butylphenol, 4-n-butyl-2,6-di-tert-butylphenol, 4-tert-amylphenol, 2,6-diisopropylphenol, 2,6-di-tert-butyl-α-dimethylamino-p-cresol, and the like. Other suitable types of antioxidants include amine antioxidants such as cyclohexyldimethylamine, N,N'-di-sec-butyl-p-phenylene diamine, N,N'-diisopropyl-p-phenylene diamine, 4-isopropylaminodiphenylamine, etc.; phosphite esters such as triphenyl phosphite, trisnonylphenylphosphite, triisooctyl phosphite, triisodecyl phosphite, trilauryl phosphite, etc.; sulfur-containing antioxidants such as 4,4'-thiobis(2-methyl-6-tert-butylphenol), dilauryl thiodipropionate, distearyl thiodipropionate, etc.; and other similar substances. Amounts of antioxidant in the range of about 1 to about 10 pounds per thousand barrels are typical. However, greater or lesser amounts can be used whenever deemed necessary or desirable.

Various conductivity improvers suitable for use in the fuels of this invention are available in the marketplace. These include ASA-3 marketed by Royal Lubricants Co., Roseland N.J., and Stadis 450 marketed by E. I. dupont de Nemours Co., Wilmington Del. Typically, conductivity improvers are additives that can be dissolved in the fuel in the amount necessary to increase the fuel conductivity to within a suitable range, such as between about 50 and about 600 pS/m as determined by ASTM D-2624. For further detail concerning conductivity improvers which can be utilized in the practice of this invention, see U.S. Pat. Nos. 3,449,097; 3,455,665; 3,578,421; 3,652,238; 3,676,647; 3,674,450; 3,784,362; 3,917,466; 4,029,480; 4,113,443; 4,252,542; 4,259,087; 4,333,741; 4,356,002 and 4,416,668. The disclosures of each of these patents is incorporated herein by reference.

Metal deactivators which can be used in the fuels of this invention include N,N'-disalicylidene-1,2-propanediamine, N,N'-disalicylidene-1,2-cyclohexanediamine, N,N'-disalicylidene-1,2-ethanediamine, N,N"-disalicylidene-N'-methyl-dipropylenetriamine. 8-hydroxyquinoline, ethylene diaminetetracarboxylic acid, acetyl-acetone, octylacetoacetate, and like substances. Thiadiazoles such as HITEC® 314 additive (Ethyl Petroleum Additives, Inc.; Ethyl Petroleum Additives, Ltd.; Ethyl Canada Ltd.; Ethyl S. A.) can also be used for this purpose. Amounts of up to about 2 pounds of metal deactivator per thousand barrels are ordinarily sufficient, but higher concentrations can be used whenever necessary or desirable.

Icing inhibitor additives that can be used include, for example, alcohols, glycols, monocarboxylic acid esters of polyoxyalkylene glycols, and nitroketonized amides. Amounts of up to about 50 pounds per thousand barrels are usually sufficient.

Detergent/dispersant additives which are suitable for use in the fuels of this invention include amides and imides especially succinimides (e.g., U.S. Pat. Nos. 3,471,458; 3,655,351; 4,596,663; and 4,744,798); mono- and polycarboxylic acid esters especially succinic acid esters (e.g., U.S. Pat. Nos. 3,639,242; 3,708,522; and 4,596,663); carbamates (e.g., U.S. Pat. No. 3,652,240); hydrocarbyl polyamines (e.g., U.S. Pat. Nos. 3,753,670 and 3,756,793); and hydrocarbyl polyether polyamines (e.g., U.S. Pat. No. 4,778,481).

A few of the numerous other additives that can be employed in the fuels of this invention are the smoke and/or particulate suppressant additives of U.S. Pat. Nos. 3,817,720; 4,240,801; 4,549,884; 4,891,049; 4,904,279; 4,908,045; and 4,920,691; the rust and/or corrosion inhibitors of U.S. Pat. No. 4,148,605 and 4,874,395; the cetane improvers of U.S. Pat. Nos. 4,280,819; 4,405,333; 4,405,334; 4,405,335; 4,406,665; 4,417,903; 4,420,311; 4,421,522; 4,448,587; 4,457,763; 4,473,378; 4,522,630; 4,549,883; 4,723,963; 4,746,326; and 4,943,303; the engine cleanliness or deposit control additives of U.S. Pat. Nos. 4,482,353; 4,482,355; 4,482,356; 4,482,357; 4,541,838; 4,549,885; 4,553,979; 4,588,415; 4,588,416; 4,588,417; 4,592,761; 4,594,077; 4,604,102; 4,613,341; 4,623,360; 4,623,361; 4,623,362; 4,623,363; 4,626,259; 4,652,272; and 4,964,879; the cold flow improvers/pour point depressants of U.S. Pat. Nos. 4,512,775; 4,575,526; 4,613,342; and 4,845,157; the friction reducing additives of U.S. Pat. Nos. 4,692,257; 4,816,037; 4,830,636; and 4,867,752; the fuel conditioners of U.S. Pat. No. 4,753,661; the color stabilizers of U.S. Pat. Nos. 4,775,389 and 4,778,480; the combustion improvers of U.S. Pat. Nos. 4,857,073 and 4,877,414; the stabilizers of U.S. Pat. Nos. 4,239,497; 4,444,566; 4,460,379; 4,460,381; 4,482,354; 4,509,952; 4,689,051; and 4,871,374; the compatibilizers of U.S. Pat. No. 4,881,945; and the biocides of U.S. Pat. No. 4,968,323.

The disclosures of each and every one of the above patents is incorporated herein by reference.

As used herein the term "fuel-soluble" means that the composition in the particular base fuel employed dissolves at 25° C. to at least the minimum concentration herein specified.

This invention is susceptible to considerable variation in its practice. Thus this invention is not intended to be limited by the specific exemplifications set forth hereinabove. Rather, what is intended to be covered is within the spirit and scope of the appended claims.

What is claimed is:

1. A middle distillate engine fuel composition, which composition comprises a major proportion of a hydrocarbonaceous middle distillate fuel and a minor wear-inhibiting amount of a combination of (i) at least one oil-soluble aryl phosphate of the formula

wherein each R is, independently, phenyl or an alkyl-substituted phenyl group; and (ii) at least one oil-soluble aryl pholyphosphate of the formula

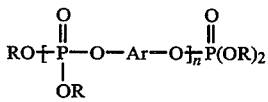

wherein each R is, independently, phenyl or an alkyl-substituted phenyl group, Ar is m-phenylene or an alkyl-substituted m-phenylene group, and n is a whole or fractional number from 1 to 4; said combination containing from 2 to 30% by weight of component.

2. A composition as claimed in claim 1 wherein each R in compounds (i) and (ii) is phenyl and Ar is m-phenylene.

3. A composition as claimed in claim 1 wherein each R in compounds (i) and (ii) is an alkyl phenyl group in which the alkyl group contains from 2 to 10 carbon atoms.

4. A composition as claimed in claim 1 wherein each R in compounds (i) and (ii) is nonylphenyl.

5. A composition as claimed in claim 1 wherein each R in compounds (i) and (ii) is phenyl or a nonylphenyl group.

6. A composition as claimed in claim 1 wherein said fuel additionally contains a minor effective amount of at least one fuel-soluble antioxidant.

7. A composition as claimed in claim 1 wherein said fuel additionally contains a minor effective amount of at least one fuel-soluble conductivity improver.

8. A composition as claimed in claim 1 wherein said fuel additionally contains a minor effective amount of at least one fuel-soluble metal deactivator.

9. A composition as claimed in claim 1 wherein said fuel additionally contains a minor effective amount of at least one fuel-soluble icing inhibitor additive.

10. A composition as claimed in claim 1 wherein said fuel additionally contains a minor effective amount of at least one fuel-soluble antioxidant and a minor effective amount of at least one fuel-soluble conductivity improver.

11. A composition as claimed in claim 1 wherein said fuel additionally contains a minor effective amount of at least one fuel-soluble antioxidant and a minor effective amount of at least one fuel-soluble metal deactivator.

12. A composition as claimed in claim 1 wherein said fuel additionally contains a minor effective amount of at least one fuel-soluble antioxidant, a minor effective amount of at least one fuel-soluble conductivity improver, and a minor effective amount of at least one fuel-soluble metal deactivator.

13. A composition as claimed in claim 1 wherein at least 50% by weight of said aryl pholyphosphate has the formula of claim 1 wherein n is 1.

14. A composition as claimed in claim 1 wherein each R in compounds (i) and (ii) is phenyl and at least 50% by weight of said aryl polyphosphate is m-phenylenebis(diphenyl phosphate).

15. A composition as claimed in claim 1 wherein said combination is formed by (a) reacting from about 1.9 to about 2.1 moles of phenol or alkyl-substituted phenol with one mole of phosphoryl trihalide, and (b) reacting the intermediate product formed in (a) with from about 0.45 to about 0.55 moles of resorcinol or alkyl-substituted resorcinol per mole of phosphoryl trihalide employed in (a), said reactions being conducted in the presence of a Lewis acid catalyst or an at least stoichiometric amount of a hydrogen halide acceptor.

16. A composition in accordance with claim 15 wherein in (a) said phenol or alkyl-subsituted phenol is added to a solution of said phosphoryl trihalide, and in (b) said resorcinol or alkyl-substituted resorcinol is added to the intermediate product formed in (a).

17. A composition in accordance with claim 15 wherein in (a) a solution of said phenol or alkyl-substituted phenol and hydrogen halide acceptor is added to a solution of said phosphoryl trihalide, and in (b) a solution of said resorcinol or alkyl-substituted resorcinol and hydrogen halide acceptor is added to the intermediate product formed in (a).

18. A composition in accordance with claim 15 wherein the reactions of (a) and (b) are performed in the presence of a Lewis acid catalyst.

19. A composition in accordance with claim 18 wherein in (a) said phenol or alkyl-substituted phenol is added to a solution of said phosphoryl trihalide, and in (b) said resorcinol or alkyl-substituted resorcinol is added to the intermediate product formed in (a).

20. A composition as claimed in claim 1 wherein said combination is formed by (a) reacting from about 0.45 to about 0.55 moles of resorcinol or alkyl-substituted resorcinol with one mole or phosphoryl trihalide, and (b) reacting the intermediate product formed in (a) with from about 1.9 to about 2.1 moles of phenol or alkyl-substituted phenol per mole of phosphoryl trihalide employed in (a), said reactions being conducted in the presence of a Lewis acid catalyst or an at least stoichiometric amount of a hydrogen halide acceptor.

21. A composition in accordance with claim 20 wherein in (a) said resorcinol or alkyl-substituted resorcinol is added to a solution of said phosphoryl trihalide, and in (b) said phenol or alkyl-substituted phenol is added to the intermediate product formed in (a).

22. A composition in accordance with claim 20 wherein in (a) a solution of said resorcinol or alkyl-substituted resorcinol and hydrogen halide acceptor is added to a solution of said phosphoryl trihalide, and in (b) a solution of said phenol or alkyl-substituted phenol and hydrogen halide acceptor is added to the intermediate product formed in (a).

23. A composition in accordance with claim 20 wherein the reactions of (a) and (b) are performed in the presence of a Lewis acid catalyst.

24. A composition in accordance with claim 23 wherein in (a) said resorcinol or alkyl-substituted resorcinol is added to a solution of said phosphoryl trihalide, and in (b) said phenol or alkyl-substituted phenol is added to the intermediate product formed in (a).

* * * * *